United States Patent
Bahmanyar et al.

(10) Patent No.: US 10,988,034 B2
(45) Date of Patent: Apr. 27, 2021

(54) ANTENNA FOR AN IMPLANTABLE DEVICE

(71) Applicant: IP2IPO INNOVATIONS LIMITED, London (GB)

(72) Inventors: Mohammad Reza Bahmanyar, London (GB); Christopher Neil McLeod, London (GB); Olive H Murphy, London (GB)

(73) Assignee: IP2IPO INNOVATIONS LIMITED, London (GB)

(*) Notice: Subject to any disclaimer, the term of this patent is extended or adjusted under 35 U.S.C. 154(b) by 105 days.

(21) Appl. No.: 16/334,616

(22) PCT Filed: Sep. 20, 2017

(86) PCT No.: PCT/GB2017/052801
§ 371 (c)(1),
(2) Date: Mar. 19, 2019

(87) PCT Pub. No.: WO2018/055366
PCT Pub. Date: Mar. 29, 2018

(65) Prior Publication Data
US 2019/0343388 A1 Nov. 14, 2019

(30) Foreign Application Priority Data
Sep. 21, 2016 (GB) ..................... 1616096

(51) Int. Cl.
*A61B 5/00* (2006.01)
*B60L 15/20* (2006.01)
(Continued)

(52) U.S. Cl.
CPC ........ *B60L 15/2045* (2013.01); *A61B 5/0031* (2013.01); *A61B 5/036* (2013.01);
(Continued)

(58) Field of Classification Search
CPC ...... B60L 15/2045; B60L 53/80; B60L 58/10; B60L 58/21; B60L 58/22; B60L 58/20;
(Continued)

(56) References Cited

U.S. PATENT DOCUMENTS 10,016,133 B2 * 7/2018 DeHennis ............ A61B 5/1455
2002/0123776 A1 9/2002 Von et al.
(Continued)

FOREIGN PATENT DOCUMENTS

EP 2296752 A2 3/2011
WO 2007002185 A2 1/2007
(Continued)

OTHER PUBLICATIONS

Great Britain Examination Report for Appl No. GB1715279.4 dated Oct. 29, 2019, 2 pages.
(Continued)

*Primary Examiner* — Scott M. Getzow
(74) *Attorney, Agent, or Firm* — Maine Cernota & Rardin (57) ABSTRACT

An implantable device for deployment inside a human or animal body, the device comprising at least one sensing component arranged to respond to an electrical signal having a known frequency band and at least one antenna comprising at least one antenna pole connected to the at least one sensing component, the antenna pole comprising at least one helical coil and a connecting stem.

3 Claims, 9 Drawing Sheets (51) Int. Cl.
*A61B 5/03* (2006.01)
*A61B 5/07* (2006.01)
B60L 53/80 (2019.01)
*A61B 5/0215* (2006.01)

(52) U.S. Cl.
CPC .............. *A61B 5/076* (2013.01); *A61B 5/686* (2013.01); *A61B 5/6882* (2013.01); B60L 53/80 (2019.02); *A61B 5/02158* (2013.01); *A61B 5/6861* (2013.01); *A61B 5/6876* (2013.01); *A61B 2560/0219* (2013.01); *A61B 2560/0247* (2013.01); *A61B 2560/0462* (2013.01); *A61B 2562/162* (2013.01)

(58) Field of Classification Search
CPC ............ B60L 2240/62; B60L 2260/54; B60L 2240/60; B60L 2260/52; A61B 5/0031; A61B 5/036; A61B 5/076; A61B 5/686; A61B 5/6882; A61B 5/6862; A61B 5/02158; A61B 5/6861; A61B 5/6876; A61B 2560/0219; A61B 2560/0247; A61B 2560/0462; A61B 2562/162; A61B 2562/0204; A61B 2562/04; A61B 5/026; A61B 2562/0247; A61B 5/0215; A61B 5/7203; A61B 2562/12; A61B 5/6846; Y02T 10/64; Y02T 10/70; Y02T 90/16; Y02T 10/7072; Y02T 10/72; A61N 1/37229
See application file for complete search history.

(56) References Cited

U.S. PATENT DOCUMENTS

| | | |
|---|---|---|
| 2005/0080346 A1 | 4/2005 | Gianchandani et al. |
| 2006/0247712 A1* | 11/2006 | Fuller ................ A61N 1/37229 607/32 |
| 2007/0288065 A1 | 12/2007 | Christman et al. |
| 2009/0243956 A1 | 10/2009 | Keilman et al. |
| 2010/0019985 A1 | 1/2010 | Bashyam et al. |
| 2010/0179449 A1 | 7/2010 | Chow et al. |
| 2010/0262036 A1 | 10/2010 | Najafi et al. |
| 2014/0214120 A1 | 7/2014 | Simon et al. |
| 2015/0342470 A1 | 12/2015 | Cros et al. |
| 2016/0022447 A1 | 1/2016 | Kim et al. |
| 2016/0045316 A1 | 2/2016 | Braido et al. |
| 2018/0050206 A1* | 2/2018 | Waldhauser ........... A61N 1/025 |

FOREIGN PATENT DOCUMENTS

| | | |
|---|---|---|
| WO | 2009073615 A1 | 6/2009 |
| WO | 2010051217 A1 | 5/2010 |
| WO | 2010081134 A1 | 7/2010 |
| WO | 2013046039 A2 | 4/2013 |
| WO | 2014159991 A1 | 10/2014 |
| WO | 2018055366 A1 | 3/2018 |

OTHER PUBLICATIONS

Amendments filed in United Kingdom Patent Application No. 1715279.4 submitted to UKIPO dated Feb. 28, 2020, 21 pages.
Great Britain Examination Report for Appl No. GB1715279.4 dated Jul. 24, 2019, 2 pages.
PCT Written Opinion for Appl No. PCT/GB2017/052801 dated Jan. 8, 2018, 12 pages.
PCT Search Report for Appl No. PCT/GB2017/052801 dated Jan. 8, 2018, 7 pages.
Great Britain Examination Report for Appl No. GB1715279.4 dated Jan. 18, 2019, 6 pages.
Great Britain Combined Search and Examination Report for Appl No. GB1715279.4 dated Apr. 25, 2018, 5 pages.

* cited by examiner

ANTENNA FOR AN IMPLANTABLE DEVICE

RELATED APPLICATIONS

This application is a national phase application filed under 35 USC § 371 of PCT Application No. PCT/GB2017/052801 with an International filing date of Sep. 20, 2017 which claims priority of GB Patent Application 1616096.2 filed Sep. 21, 2016. Each of these applications is herein incorporated by reference in their entirety for all purposes. This application is related to PCT Application No. PCT/GB2017/052802 with an International filing date of Sep. 20, 2017 which claims priority of GB Patent Application 1616090.5 filed Sep. 21, 2016; PCT Application No. PCT/GB2017/052804 with an International filing date of Sep. 20, 2017 which claims priority of GB Patent Application 1616096.2 filed Sep. 21, 2016; PCT Application No. PCT/GB2017/052834 with an International filing date of Sep. 21, 2017 which claims priority of GB Patent Application 1616092.1 filed Se. 21, 2016; and PCT Application No. PCT/GB2017/053313 with an International filing date of Nov. 2, 2017 which claims priority of GB Patent Application 1618508.4 filed Nov. 2, 2016; each of these applications is herein incorporated by reference in their entirety for all purposes.

FIELD

The present invention relates to implantable devices for implanting into the human or animal body. In particular, the invention relates to an antenna for an implantable device.

BACKGROUND

Such devices may generally be implanted into any part of the body and include, for example, into the vasculature of the human or animal body. Where there is a need for long-term monitoring of patients the repeated use of invasive measurements increases the risk of injury and can ultimately lead to the physician deciding that such a procedure is too risky to undertake. Medical technology is progressing rapidly, and with it has increased the range of implantable devices available for providing a variety of internal measurements of the vital signs of a patient to a physician.

Implantable devices are preferred for taking internal measurements, as repeatedly inserting and removing devices can be detrimental to a patient's health. Once implanted, the device can provide information over a long period without further risk each time they are used. Communication with implants can be achieved through inductive coupling or through a radio-frequency link from a transmitter/receiver located outside the patient's body. Other means of communication are desirable.

SUMMARY

Aspects and embodiments of an implantable device are set out in the appended claims. These and other aspects and embodiments of the implantable device are also described herein.

Described herein is an implantable device for deployment inside a human or animal body, the device comprising: at least one sensing component arranged to respond to an electrical signal having a known frequency band: and at least one antenna arranged to be in electrical communication with the at least one sensing component, the antenna comprising at least one antenna pole comprising at least one helical coil and a connecting stem. The helical coil may provide a distal portion of the antenna (e.g. near its tip) whereas the stem may provide the proximal part of the antenna, e.g. nearer to the device. The stem may be straight.

Optionally, the helical coil and the stem may be arranged so that the bandwidth of the at least one antenna encompasses the known frequency band. Optionally, the diameter of the helical coil may be selected so that the bandwidth of the at least one antenna encompasses the known frequency band. Optionally, the pitch of the coils in the helical coil may be selected so that the bandwidth of the at least one antenna encompasses the known frequency band. Optionally, the number of turns in the helical coil may be selected so that the bandwidth of the at least one antenna encompasses the known frequency band.

Optionally, at least one of the thickness of the coil wire and the thickness of the stem may be selected so that the bandwidth of the at least one antenna encompasses the known frequency band. Optionally, at least one of the length of the helical coil or stem may be selected so that the bandwidth of the at least one antenna encompasses the known frequency band. Optionally, the relative lengths of the helical coil and stem may be selected so that the bandwidth of the at least one antenna encompasses the known frequency band. Optionally, the material of the at least one antenna pole may be selected so that the bandwidth of the at least one antenna encompasses the known frequency band.

Optionally, the at least one antenna pole may be at least partially disposed within a sleeve, arranged at least partially to insulate the at least one antenna pole. Optionally, the material of the at least one insulating sleeve may be selected so that the bandwidth of the at least one antenna encompasses the known frequency band. Optionally, the thickness of the at least one insulating sleeve may be selected so that the bandwidth of the at least one antenna encompasses the known frequency band. Optionally, the at least one insulating layer may comprise a plurality of layers. Optionally, at least one of the number of layers and the (one or more) materials used in the layers of the at least one insulating sleeve may be selected so that the bandwidth of the at least one antenna encompasses the known frequency band.

The at least one sensing component may comprise a first sensing component and a second sensing component. Optionally, the first sensing component is tuned to respond to electrical signals of a first known frequency band and the second sensing component is tuned to respond to electrical signals of a second known frequency band. The first known frequency band may be different to the second known frequency band. The sensing components may each comprise pressure transducers for sensing intravascular pressure. Examples of such transducers may include acoustic wave devices, such as surface acoustic wave (SAW) and bulk acoustic wave (BAW). These devices may be arranged so that variations in intravascular pressure cause mechanical stress and/or strain in a piezoelectric substrate. These variations in stress and/or strain can cause corresponding variations in acoustic wave properties through the substrate which may be sensed using structures such as interdigitated transducers.

Also described herein is an implantable device for deployment inside a human or animal body, the device comprising: at least two sensing components; and at least one antenna arranged to be in electrical communication with said at least two sensing components, wherein each sensing component is arranged to respond to an electrical signal at a different known frequency within the bandwidth of the at least one antenna.

Optionally, each sensing component may be arranged to be energised selectively by transmitting to the device a specific electrical signal within the bandwidth. The one or more sensing components may be at least in part disposed within a housing. Optionally, the housing may comprise a crystalline material, for example a piezoelectric material, optionally comprising quartz. The one or more sensing components may be encapsulated within the housing.

An anchor may be provided for securing the device within a vascular lumen of a human or animal body, for example wherein the anchor includes at least one strut for securing the anchor to the device or a housing of the device.

Also described herein is an implantable device, comprising: a housing arranged to house at least one sensing component; at least one antenna pole arranged to be in electrical communication with the at least one sensing component, the at least one antenna pole being external to the housing and having a stem for securing to the housing; and an anchor for securing the device within a vascular lumen of a human or animal body, the anchor including at least one strut for securing in a channel within the housing. It will be appreciated in the context of the present disclosure that the at least one antenna pole may be a part of an antenna comprising two or more such poles, or comprising an antenna pole and a conductive structure arranged to function as a ground plane for that antenna pole. The at least one antenna pole and the at least one strut of the anchor are arranged to reduce signal losses in the at least one antenna due to the at least one strut of the anchor.

Optionally, the at least one strut of the anchor is spaced from the at least one antenna pole by a distance that is at least equal to the thickness of the at least one strut, for example wherein the at least one strut has a thickness of at least 0.5 mm.

The at least one strut of the anchor may arranged to deflect away from the at least one antenna pole. The at least one strut of the anchor is divergent from the at least one antenna pole. The at least one strut of the anchor and the at least one antenna pole may be in substantially the same plane. The at least one strut of the anchor is arranged to diverge or deflect at an angle of at least 15 degrees relative to the at least one antenna pole.

The anchor may comprise two struts for securing in one or more channels within the housing. The struts may be arranged in a substantially parallel configuration, at least in part. Alternatively, the struts may be arranged to diverge away from each other. The struts may be arranged to deflect away from the axis of the at least one antenna pole relative to the housing. The struts may be arranged to deflect in different directions. The struts may be arranged to deflect in substantially opposing directions.

The at least one antenna may comprise a first antenna pole and a second antenna pole. The first antenna pole and the second antenna pole may be arranged to extend in different directions. The first antenna pole and second antenna pole may be arranged to be substantially coaxial. The first antenna pole and second antenna pole may be arranged to be substantially non-coaxial, or example wherein the second antenna pole is provided along an axis that is offset from the axis of the first antenna pole. The first antenna pole and second antenna pole may be arranged to be generally asymmetrical.

The at least one antenna pole may be at least partially disposed within a sleeve. Furthermore, the at least one antenna pole may be completely enclosed within the sleeve. The sleeve may be arranged to at least partially insulate the at least one antenna pole from surrounding intravascular fluid in which it may be immersed when implanted. The sleeve may comprise a dielectric material, for example polyurethane.

An implantable device and/or an antenna for such a device substantially as described herein and/or as illustrated in the accompanying drawings may also be provided.

The term bandwidth is used herein to describe the frequency band which the antenna is designed to operate with. It will be appreciated in the context of the present disclosure that this may be defined by any appropriate measure. For example, the antenna return loss is a logarithmic ratio measured in dB that compares the power reflected by the antenna to the power that is fed into the antenna from a transmission line. The bandwidth of an antenna may refer to the range of frequencies over which the antenna's return loss is acceptably low. For example, this may be defined as the band of frequencies about the minimum return loss which exhibit a less than 3 dB increase in return loss from that minimum. As another example, it will be appreciated in the context of the present disclosure that impedance mismatches may give rise to standing waves along any transmission line, and in antenna in particular. Another parameter of an antenna is the so called standing wave ratio, SWR. The SWR may be defined as the ratio of a partial standing wave's amplitude at an antinode (maximum) to the amplitude at a node (minimum) along the line. Return loss may also be expressed in relation to this SWR, viz.

$$\text{Return Loss (in dB)} = 20\log_{10}\frac{SWR}{SWR-1}$$

It will thus be appreciated in the context of the present disclosure that the bandwidth may be defined with reference to the SWR—for example it may be the frequency band throughout which the SWR is less than 2:1.

BRIEF DESCRIPTION OF THE DRAWINGS

Aspects and embodiments will now be described by way of example only, with reference to the accompanying figures, in which.

DETAILED DESCRIPTION

FIGS. 1, 2, 3A, 3B and 3C illustrate various views of the parts which make up an exemplary implantable device 101, suitable for implanting into a human or animal body. In each figure the same numbers refer to the same parts, and the following description of the device refers in general to this set of Figures.

Figure 1:
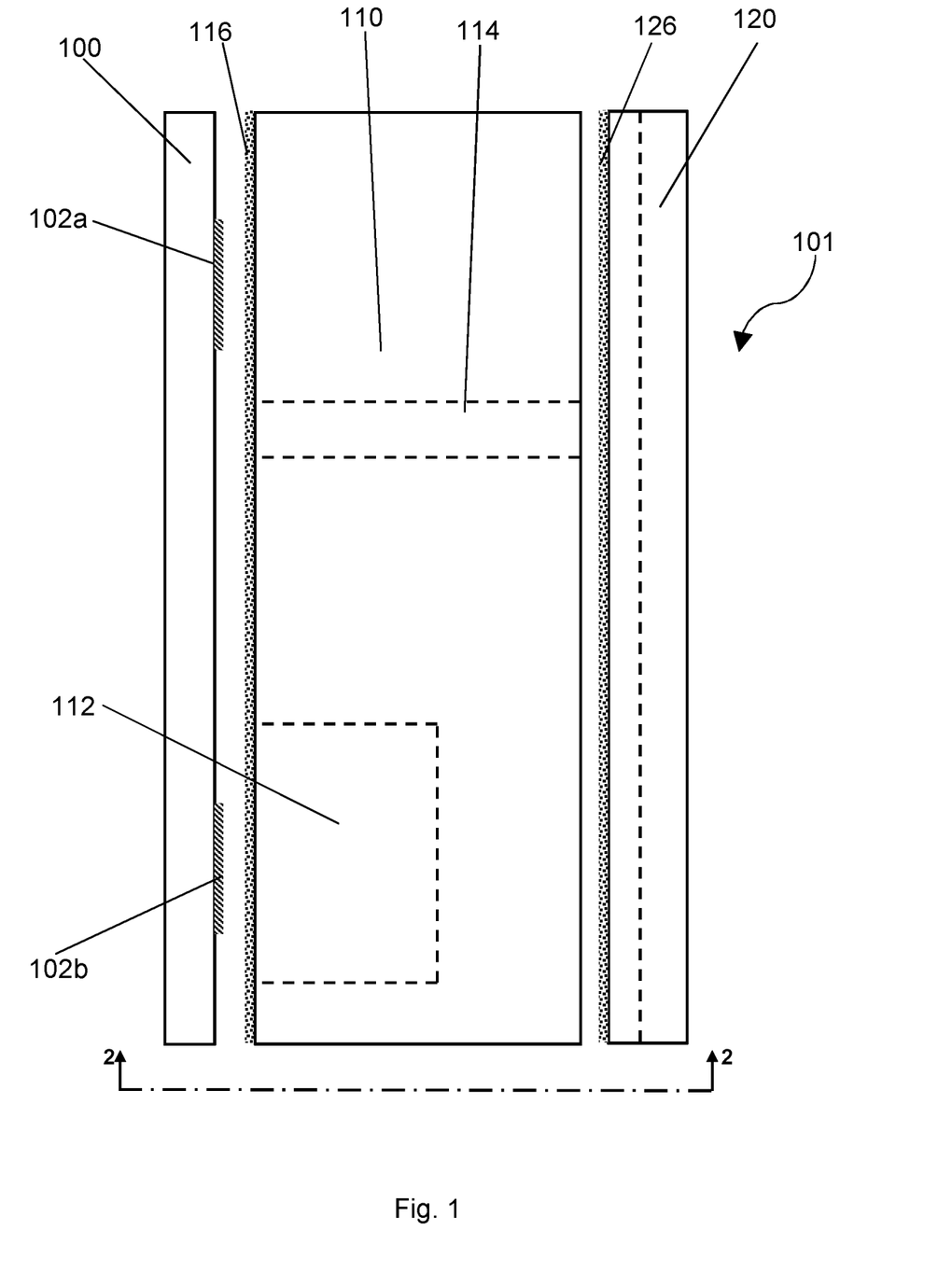
FIG. 1 shows a side view of an implantable device.
Figure 2:
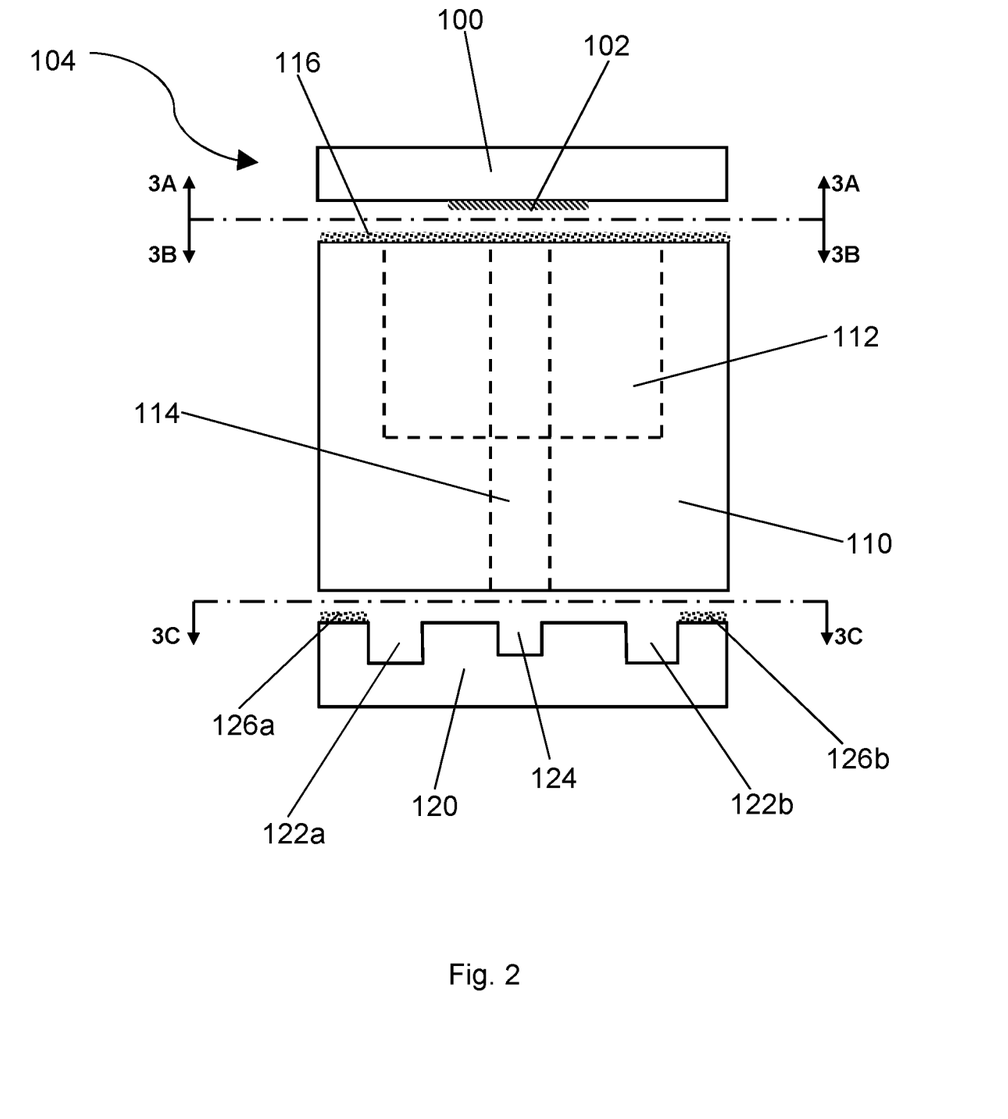
FIG. 2 shows a front view of an implantable device, showing the view in the direction of the arrows from section line 2-2 in FIG. 1.
Figure 3A:
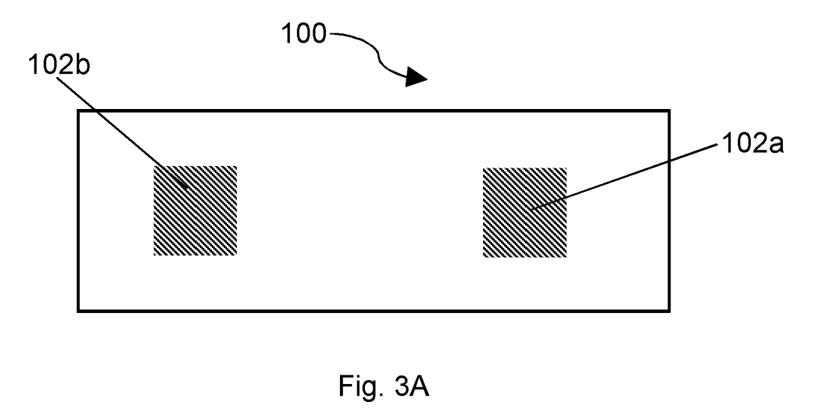
FIG. 3A shows a bottom view of part of an implantable device, showing the view in the direction of the arrows from section line 3A-3A in FIG. 2.
Figure 3B:
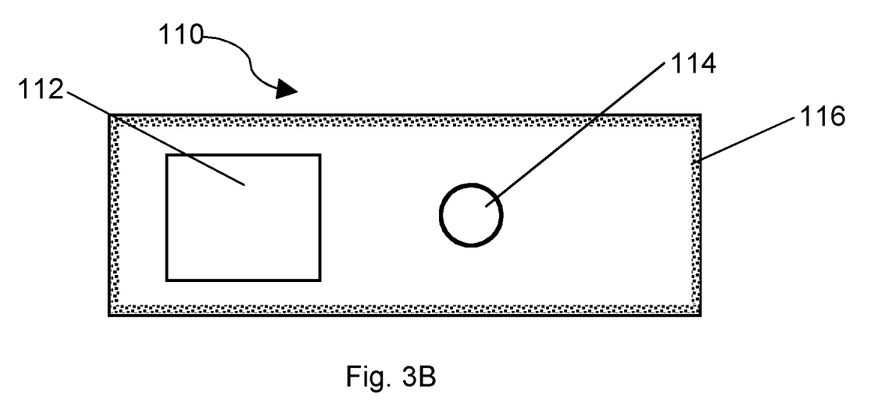
FIG. 3B shows a top view of part of an implantable device, showing the view in the direction of the arrows from section line 3B-3B in FIG. 2.
Figure 3C:
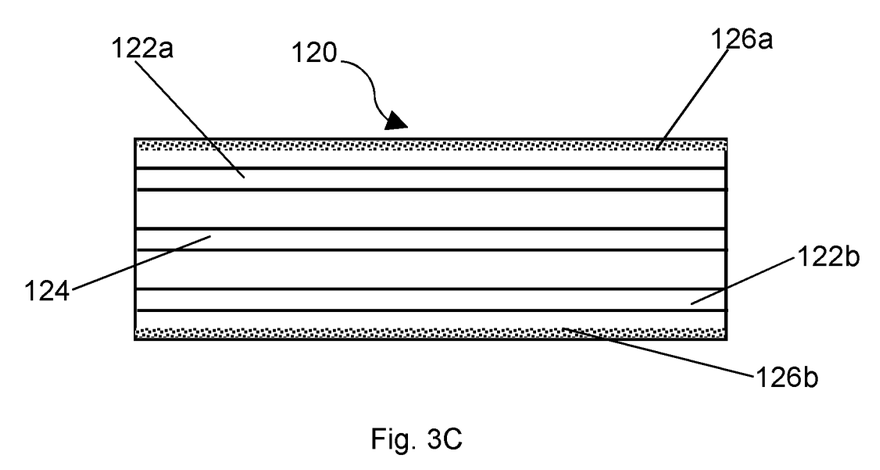
FIG. 3C shows a top view of part of an implantable device, showing the view in the direction of the arrows from section line 3C-3C in FIG. 2.

In general, FIG. 1 shows a side view of the parts, FIG. 2 shows an end view of the components, and FIGS. 3A to 3C show plan views of each of the parts. Dot-dashed lines in these Figures illustrate sectional lines, and are numbered with Figure numbers which show that view (in the direction of the arrows). Therefore, for example, the dot-dashed line labelled 2-2 in FIG. 1 illustrates the plane and direction from which the device is shown in FIG. 2.

As shown in FIG. 1, the device 101 comprises a membrane 100, a body 110 and a cap 120. An assembly comprising sensing components 102 is mounted (or carried) on the membrane 100. In the example shown, the assembly of sensing components 102 comprises two sensing components 102a and 102b arranged to respond to electrical signals. The sensing components 102 may be used for measuring various properties of their surrounding environment (as will be discussed in more detail further on).

The body 110 may comprise a crystalline material. The crystalline material may comprise a piezoelectric material. Piezoelectric materials may form part of a sensing apparatus, in conjunction with the assembly of components. The crystalline material may comprise quartz, for example.

The membrane 100 and the cap 120 are arranged on opposing sides of the body 110. Both the membrane 100 and the cap 120 are arranged to be joined to the body 110, for example by hermetic bonds 116, 126. When joined together, the membrane 100, body 110 and cap 120 may be considered to form a housing 104, for example with hermetic bonds providing a sealed housing 104. Of course, this assembly is only intended to be an example of a housing 104 that might contain sensing components 102. For example, another embodiment may not include the cap 120 such that the housing 104 comprises only the membrane 100 and the body 110.

In this exemplary housing 104, a via 114 extends through the body 110 to provide a path for the conduction of electrical signals and thereby enable communication between the sensing components 102 arranged on the membrane 100 and at least one antenna (not shown here) arranged on the cap 120.

The via 114 may be at least partially filled with a first conductor and closed by a second conductor more ductile than the first conductor, for example. The second conductor may comprise gold. The use of a more ductile material to close the via 114 helps to maintain the seal should the shape of the via 114 distort, e.g. due to thermal expansion. The via 114 may be closed by a hermetic bond to ensure that any sealed cavities in the body 110 remain hermetically sealed.

It will be appreciated in the context of the present disclosure that a sensing component may use two electrical connections, these may be provided through one or possibly two vias. This is one way to connect a sensing component to an antenna. If the antenna is a partially monopole (such as the partially helical monopole described elsewhere herein), one terminal of the sensing component may be connected to the antenna pole and the other one to a ground structure (such as a ground plane) which may be provided by the anchor struts. In such constructions, two vias may be used. In some embodiments the ground plane is provided within the device itself (e.g. within the housing). For example it may be in the form of a metalised area that is connected to one terminal of sensor(s)). In this case only one via may be needed to connect the other terminal of the sensing device to the antenna pole.

In this example of a device 101, the body 110 includes a cavity 112 extending from its upper surface towards the lower surface of the body 110, but not penetrating entirely through the body 110. When assembled, the hermetic seal 116 isolates the cavity 112 from the surrounding environment.

As shown in FIG. 2, the cap 120 has a series of three channels 122a, 122b, 124 extending along its length. Two of these channels 122a, 122b are 'fixture' channels for fixing the device 101 to an anchor (described later) to secure the device 101 within a vascular lumen, for example. The third channel 124 is a 'connection' channel arranged to be connected to at least one antenna (not shown here). Mating surfaces 126a and 126b join the cap 120 to the body 110, for example using a hermetic bond 126.

As mentioned above, the via 114 extends through the body 110 between the membrane 100 and the cap 120 and is thereby arranged to enable communication of electrical signals between the connection channel 124 (and hence a connected antenna—not shown here) and the sensing components 102 on the membrane 100.

The function of the cap 120 and the channels 122a, 122b, 124 will be described in more detail below, with reference to FIGS. 5 and 6.

As mentioned above, the sensing components 102 are arranged to respond to electrical signals, and may be used for measuring various properties of their surrounding environment. For example, when implanted in the vascular lumen of a human or animal body, the sensing components 102 may measure fluid pressure, fluid flow, local temperature, or other common measurements. The sensing components 102 may be at least partially enclosed within the housing 104 to provide protection from the external environment.

In certain embodiments, however, at least part of the sensing components 102 may be located on the outside of the housing 104 in contact with the external environment, so that comparative 'reference' measurements may be made. Furthermore, certain properties (e.g. chemical composition of the surroundings) may require direct contact between the sensing components 102 and the environment to be measured.

In this exemplary device 101 described herein, pressure is measured using interdigitated transducers (IDTs), which form part of the assembly of sensing components 102. The IDTs can be arranged so that the membrane 100 or the body 110 provides a substrate for the one or more IDTs. In particular, one or more of the IDTs may be arranged to detect a deflection of the membrane 100 as part of sensing the intravascular pressure. A specific arrangement may be that a first IDT is located in a first region of the membrane 100 which is arranged to deflect due to changes in intravascular pressure more than a second IDT located in a second region of the membrane 100. For example, the first IDT may be located in fluid communication with the cavity 112, and may deflect into the cavity 112, compressing a gas in the cavity 112 (wherein the amount of gas is already known). The second IDT may be located away from the cavity 112 on a portion of the membrane 100 arranged over a (relatively) minor cavity (not shown), and therefore is less able to deflect.

FIGS. 3A-3C plan views of the membrane 100 (FIG. 3A), the body 110 (FIG. 3B) and the cap 120 (FIG. 3C), and their respective features, described above.

Figure 4:
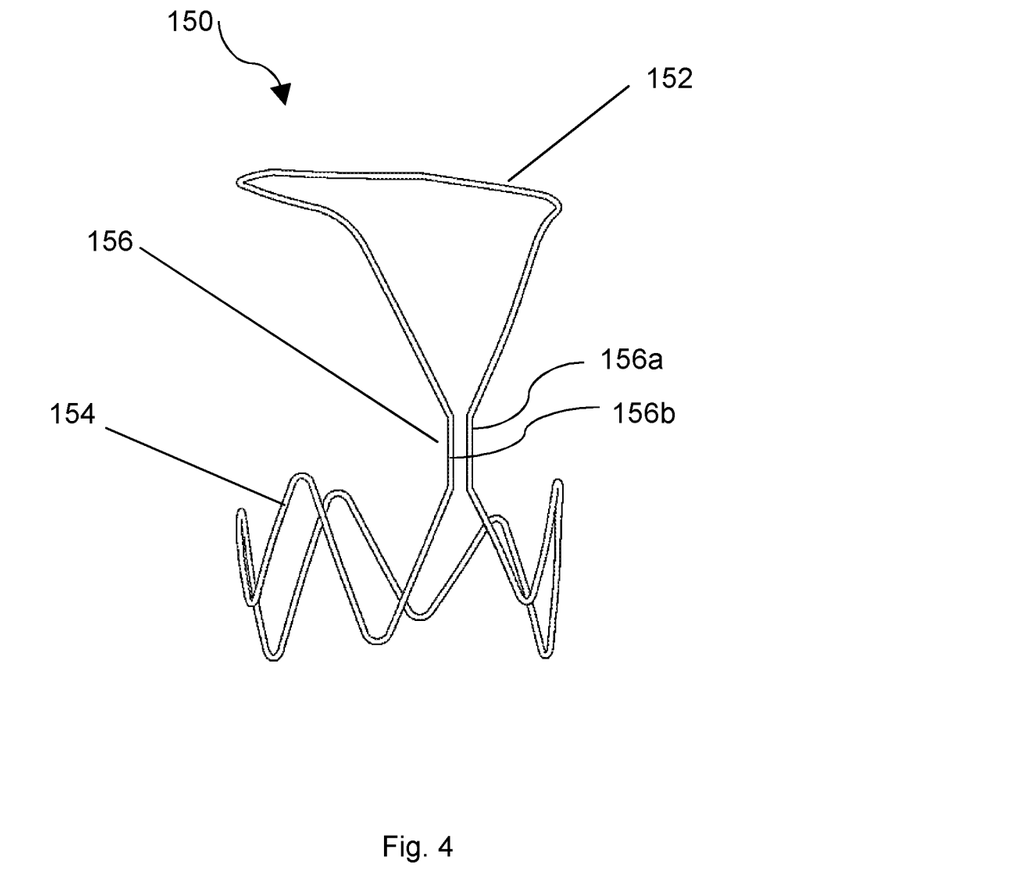
FIG. 4 shows an anchor for implanting an implantable device into a vascular lumen of a body.

Turning now to FIG. 4, there is shown an anchor 150 for supporting the device 101 in a vascular lumen of the human or animal body, for example. The anchor 150 comprises an upper portion 152, a lower portion 154 and a central portion 156. Both the upper portion 152 and the lower portion 154 are generally configured as loops arranged to contact the walls of a vascular lumen into which the anchor is inserted while not inhibiting the flow of intravascular fluids. The central portion 156 comprises two struts 156a, 156b arranged to be received by the fixing channels 122a, 122b provided in the cap 120 so as to fix the device 101 to the anchor 150.

Figure 5:
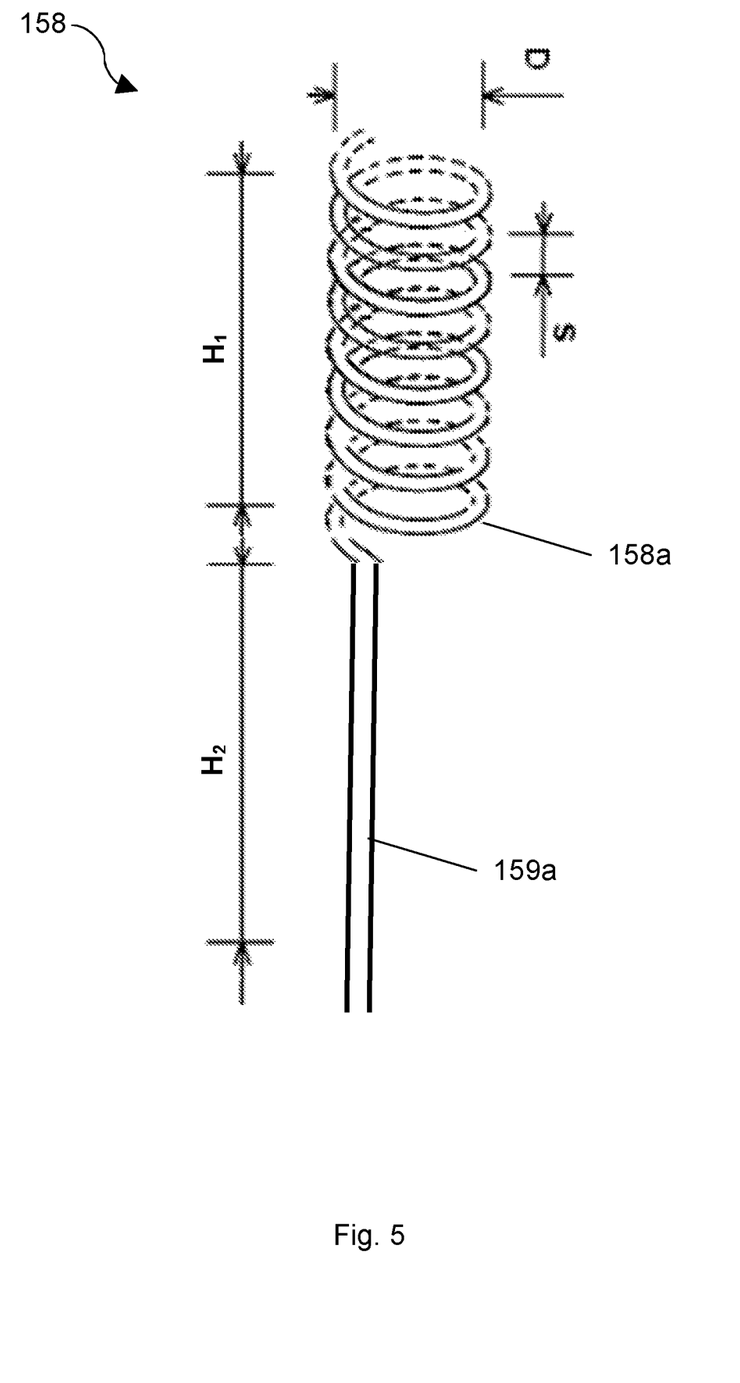
FIG. 5 shows an antenna pole for an implantable device.

FIG. 5 shows an antenna pole 158 suitable for use with the implantable device 101. The antenna pole has at least one partially helical portion 158a. The antenna pole 158 also includes a stem portion 159a, which may be straight. It may be self-supporting, for example it may be resilient. It also provides an electrical connection between the helical part 158a of the antenna pole and the connection channel 124 provided in the cap 120, in which the stem 159a of the antenna 158 may be seated. The antenna 158 has several properties, which can be varied to 'tune' it to receive (i.e. so that its bandwidth encompasses) at least one selected frequency or band of frequencies. For example it may be tuned such that the bandwidth of the at least one antenna 158 can encompasses a known frequency band of at least one sensing component 102 (this known frequency band may be any selected frequency band, and may be determined by the characteristics of that sensing component). The 'tuneable' properties include (helical) coil spacing (or 'pitch'), s; coil width (or 'thickness'), w; number of turns in the coil, n; coil height (or length), H [where H=(s+w).n]; and helical coil diameter, D. The length and thickness of the stem may also be varied, including the relative length of the stem 159a and the length of the helical antenna pole 158a. Alternatively, the pitch, s, of the helix may be measured from centre to centre of adjacent turns, n [where H=s.n].

Figure 6:
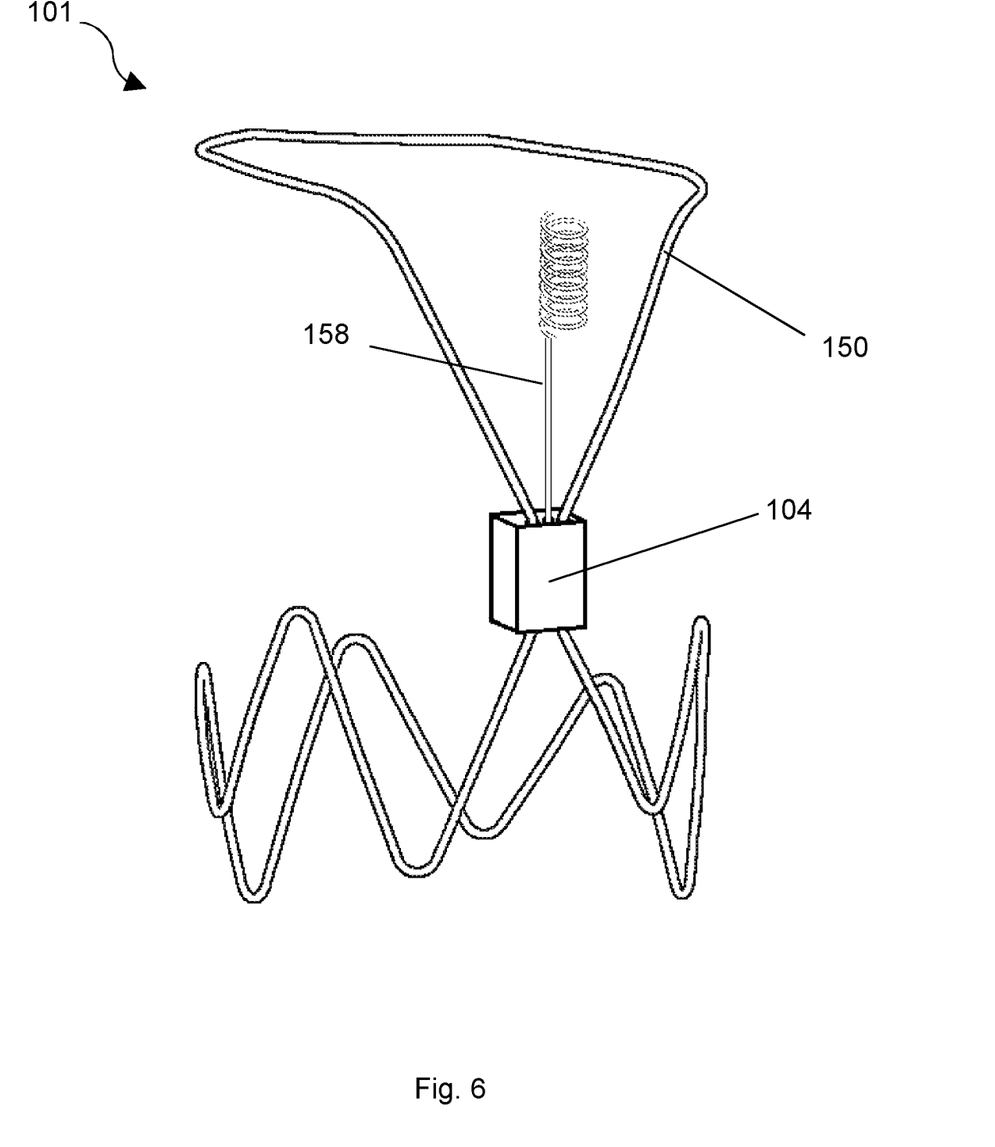
FIG. 6 shows an implantable device, having an external antenna pole, mounted on an anchor.

In FIG. 6, an example of a device 101 having an antenna 158 is shown fixed to an anchor 150, as described above. As mentioned above, the struts 156a, 156b of the central portion 156 of the anchor 150 may be received within the fixing channels 122a, 122b of the cap 120, which is then joined to the body 110, thereby fixing the device 101 to the anchor 150.

While the exemplary device 101 shown in the figures has two sensing components 102a, 102b (for example, one to provide a 'reference' measurement, to which a test measurement performed by the other can be compared), some embodiments of an implantable device (not shown) may have a single antenna in electrical communication with only one sensing component. The antenna may have both a stem and a helical coil. As described above, the stem may be straight and may join a distal helical portion of the antenna to the body of the device. The features of this structure can be selected to 'tune' (e.g. to select) the bandwidth of the antenna to encompass frequencies to which sensors carried by the device 101 may be tuned to respond.

Thus, the implantable device 101 may have at least one antenna comprising at least one antenna pole 158 arranged to be in electrical communication with at least one sensing component carried by that device. For example the at least one sensing component may be configured to be energised by an alternating electrical signal received by the at least one antenna. For example it may be connected to the antenna so that such a signal received by the antenna 158 energises the at least one sensing component.

If the antenna 158 comprises a single antenna pole 158a, then the antenna 158 may be a mono-pole and a ground plane or other conductive ground structure may be provided separately. The anchor 150 (described above), e.g. its struts may be used for this purpose. In such an arrangement, when implanted in a human or animal body the anchor 150 may be in (electrical) contact with the surrounding body tissue or it may be insulated by an insulating coating (not shown). The coating may be formed by depositing layers of different insulating materials, including oxides, nitrides and polymers.

If an implantable device 101 has two sensing components 102a, 102b and only a single antenna 158 (as shown in FIG. 6), the connection channel 124 within the cap 120 of the housing 104 may be configured to provide communication between the antenna 158 and both of the sensing components 102a, 102b, for example by way of at least one via 114 provided through the body 110, as described above.

The sensing components 102 may be configured to respond to a known frequency band (e.g. for two sensing components, a first known frequency band and a second known frequency band) within the bandwidth of the at least one antenna 158. The known frequency bands may be different to allow selective communication with only one of the sensing components 102. Thus, the bandwidth of the antenna 158 may be configured to encompass both (or all) known frequency bands to which the sensing components 102 are configured to respond.

Figure 7:
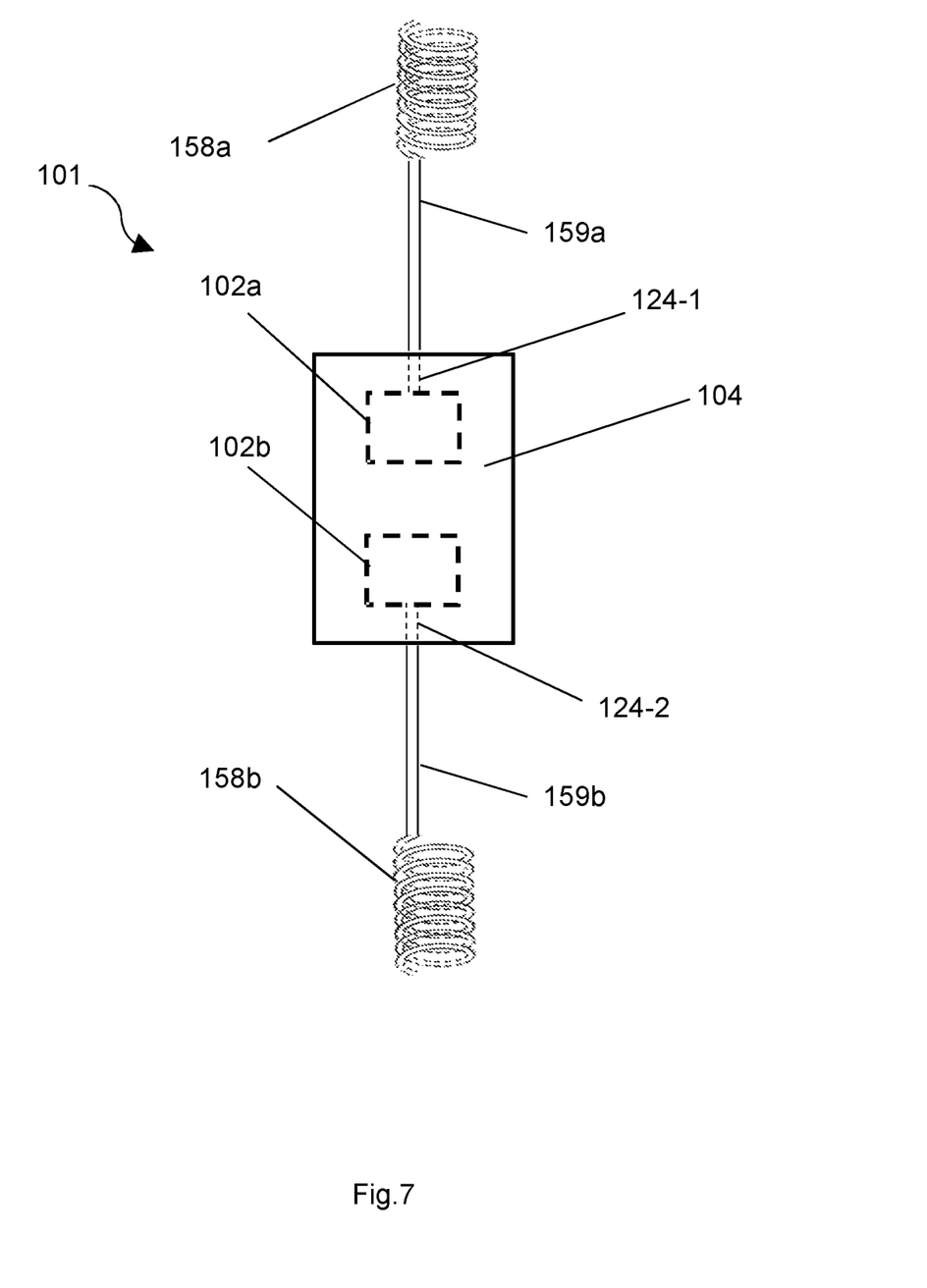
FIG. 7 shows an implantable device having two sensing components and one antenna comprising two antenna poles.

As shown in FIG. 7, an antenna 158 may comprise two antenna poles 158a, 159a, 158b, 159b each of which may be partially helical, in that they may comprise a helical portion 158a, 158b joined to the device 101 by straight connecting stem 159a, 159b. The antenna 158 can be asymmetrical—in the sense that the antenna pole 158a, 159a may be different to the other antenna pole 158b, 159b. This means that each antenna pole 158a, 159a, 158b, 159b, can have a different length, conductor thickness, and number of helical portions, e.g. each mole may have two or more helical portions joined by non-helical links which may be straight. If an insulating sleeve is provided different insulating material may be used for each pole and the material may have different thickness. Moreover, for each helix, the minor and major radii as well as the pitch and number of turns might be different. Putting different helical sections on different antenna poles 158a, 158b allows for tuning the antenna 158 to different frequency bands to produce a multiband antenna. In this way a single antenna 158 can be used to cover different sensing components 102 that work at frequency bands that are spaced far apart on the spectrum and may not be covered by a single wide frequency band (e.g. a pressure sensor at 868 MHz and a temperature sensor at 2.45 GHz).

Figure 8:
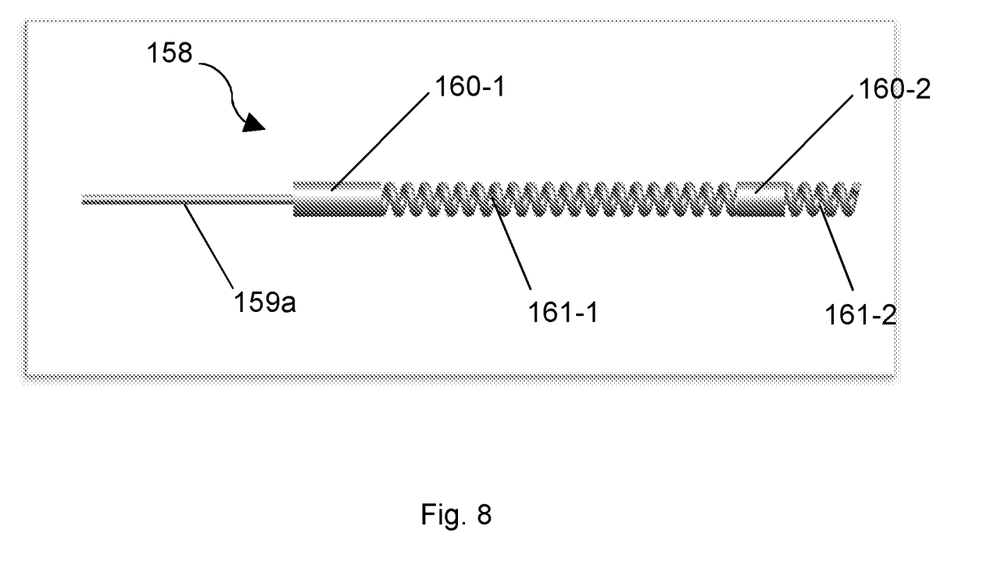
FIG. 8 shows an exemplary structure of a partially helical antenna pole.

FIG. 8 shows an example of an antenna pole 158 which is partially helical in that it includes two helical portions 161-1 and 161-2. It also includes a stem portion 159a. The first and second helical portions 161-1, 161-2 are separated by a non-helical conductive portion 160-2, which may be straight. It may be provided by a cylindrical conductor having a greater diameter than the stem. The diameter of the non-helical conductive portion 160-2 may be equal to the major diameter of the helical portions. A further non-helical portion 160-1 may join the stem portion 159a to the first helical portion 161-1. This too may be of greater diameter than the stem portion 159a and of equal diameter to the major diameter of the helical portions 161-1, 161-2. The bandwidth of the antenna may be selected (e.g. in terms of both its centre frequency and its width) by choosing the geometry of this structure. For example, the dimensions (e.g. lengths, helical pitch, and diameters) of each helical portion 161-1, 161-2 may be chosen, as may the length and diameter of each non-helical portion 160-1, 160-2. The bandwidth of the antenna may be selected by varying at least one of these parameters to provide the desired bandwidth. Thus, each antenna pole 158a, 158b may be configured to have a different bandwidth, for example each antenna pole may only encompasses the known frequency band of one of the two sensing components 102a, 102b, respectively. In some embodiments, both antenna poles have a bandwidth which encompasses the frequencies of both sensing components.

Where the device 101 has two sensing components 102, each sensing component 102a, 102b may be configured to be energised selectively by transmitting to the device 101 a specific electrical signal (e.g. an electrical signal of a known frequency band) within the bandwidth of the at least one antenna 158. In other embodiments (not shown), there may be more than two sensing components 102, and each may be configured to respond to an electrical signal of a different known frequency band within the bandwidth of the at least one antenna 158.

Figure 9:
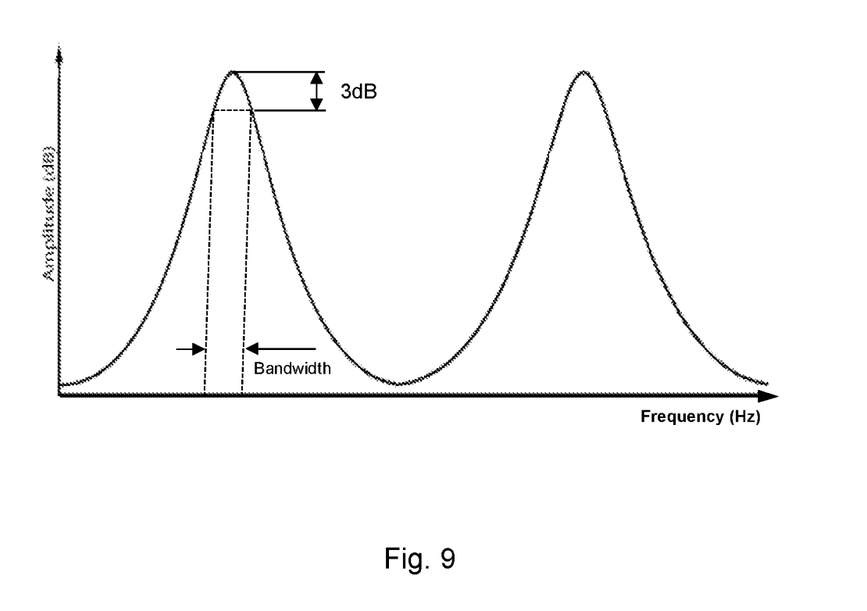
FIG. 9 shows an example of two different known frequency bands within a bandwidth of an antenna, to which sensing components may be configured to respond.

FIG. 9 is a plot of amplitude against frequency, illustrating two exemplary (different) known frequency bands within the bandwidth of at least one antenna, to which two sensing components might be configured, selectively, to respond.

FIGS. 10(a) to (d) show schematic illustrations of various different antenna arrangements which may be used for any of the implantable devices described herein, and in particular for a device having two sensing components 102a, 102b.

Figure 10A:
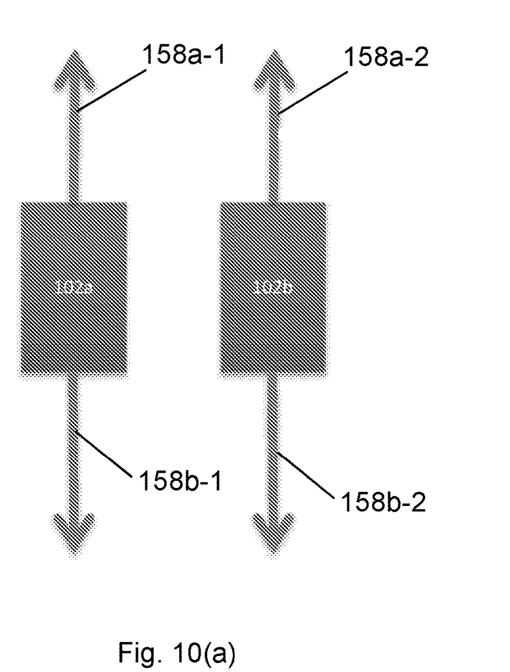
FIGS. 10(a)-10(d) show four different configurations of an antenna for an implantable device having two sensing components.

FIG. 10(a) illustrates an arrangement of two sensing components 102a, 102b. The first sensing component 102a is connected to its own antenna 158a1, 158b-1, having a first pole 158a-1 and a second pole 158b-1. Likewise, the second sensing component 102b is connected to its own antenna 158a-2, 158b-2, separate from the antenna 158a-1, 158b-1 to which the first sensing element is connected. This second antenna, may also have a first pole 158a-1 and a second pole 158b-1. Each sensing component may be connected so that a potential difference between the antenna poles can energise the sensing component 158a-1, 158b-1. It will be appreciated in the context of the present disclosure that the two antennas may be differently tuned, so that each sensing element 102a, 102b can be excited in a different frequency band from the other. This may enable the two sensing components to be excited separately, or to be excited together by the same broadband signal but to respond with a different characteristic frequency from the other sensing component. It will be appreciated in the context of the present disclosure that each sensing element 102a, 102b may also be tuned to a different frequency—e.g. configured to respond to alternating electrical signals of a different frequency band from the other sensing component. Each antenna pole 158a-1, 158b-1; 158a-2, 158b-2 may be at least partially helical as described above and may include a proximal connecting stem connecting a helical portion of the antenna pole to a device (not shown in FIG. 10a) which carries the sensing components.

Figure 10B:
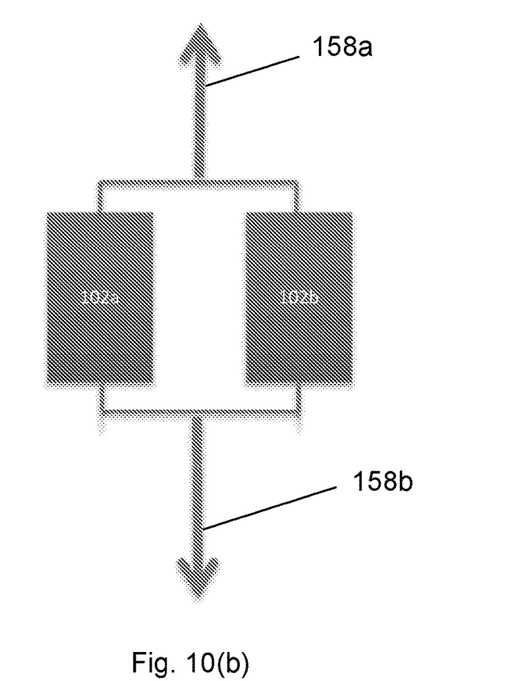

FIG. 10(b) illustrates an arrangement of two sensing components 102a, 102b with a single (shared) antenna being configured to receive electrical signals of known frequency bands for both sensing components 102a, 102b. The antenna comprises two antenna poles 158a, 158b (which may each be at least partially helical as described elsewhere herein). The two sensing components 102a, 102b are connected electrically in parallel between the two antenna poles 158a, 158b, so that a potential difference developed between the two antenna poles can be applied directly to both sensing elements 102a, 102b together. The two sensing components 102a, 102b, may be differently tuned, so that each sensing element 102a, 102b can be excited in a different frequency band from the other. In this embodiment, the bandwidth of the antenna as a whole may encompass the different frequencies to which these two sensing elements are tuned. This can enable each sensing component to be excited separately by application of an excitatory signal which falls within the bandwidth of the antenna and encompasses the frequency (or band) to which only one of the two sensing components is tuned.

Figure 10C:
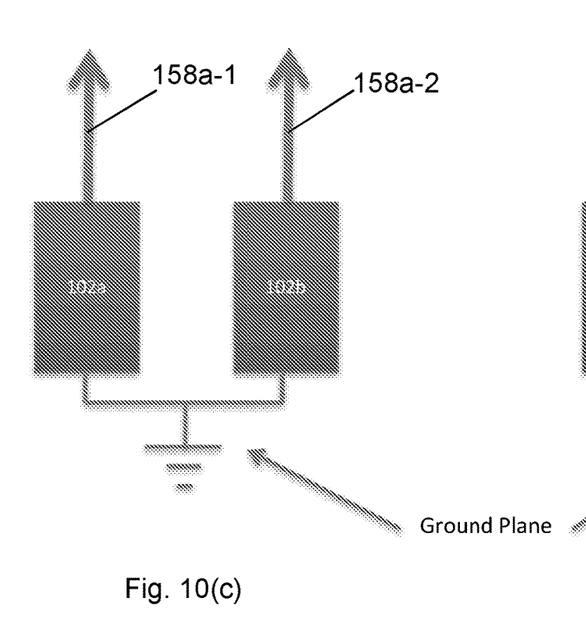

FIG. 10(c) illustrates an arrangement of two sensing components 102a, 102b, each connected in series between an antenna pole and a grounded structure such as a ground plane or other ground conductor. The first sensing component 102a is connected between a first antenna pole 158a-1 and the grounded structure. The second sensing component 102b is connected between a second antenna pole 158a-2 and the grounded structure. The first antenna pole 158a-1, and the second antenna pole 158a-2 may each be provided by a monopole (which may be at least partially helical as described elsewhere herein). Electrically this arrangement may behave as described above with reference to FIG. 10(a).

Figure 10D:
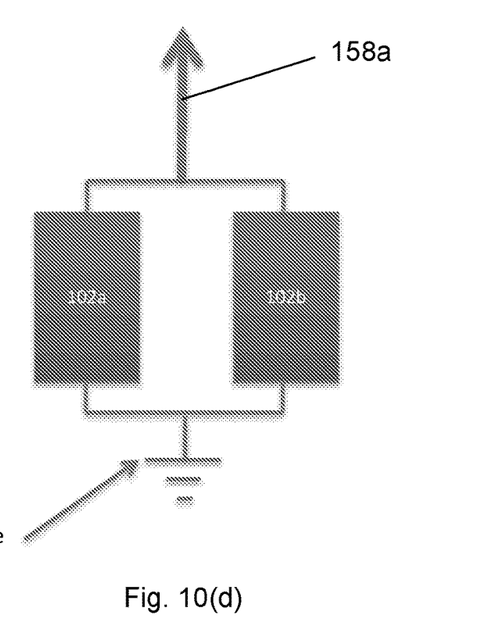

FIG. 10(d) illustrates an arrangement of two sensing components 102a, 102b with a single (shared) antenna monopole being configured to receive electrical signals of known frequency bands for both sensing components 102a, 102b. The antenna is provided by a monopole 158a (which may be at least partially helical) and a ground plane. Electrically this arrangement may behave as described above with reference to FIG. 10(b).

Although not shown, the at least one antenna pole 158a, 158b may be at least partially disposed within an insulating member, such as a sleeve (not shown). The insulation of an antenna that is designed for long term implantation should have stable desired electromagnetic properties and remain biocompatible over its lifetime. Thus, the insulating member may be coated with multiple layers to form a barrier to stop liquid/ion ingress. This can be achieved by applying multiple layers of Parylene C and oxides, for example. In general, the insulation is also a functional component of the antenna 158, the material, geometry and thickness of which can be used for tuning the antenna 158. The insulating member may comprise a dielectric material, for example polyurethane.

Although the device 101 is shown in FIG. 6 in combination with both an antenna 158 and an anchor 150, other embodiments are envisaged in which only one, or perhaps even neither, of these two components 150, 158 are provided with the device 101, depending on the desired application of the device 101. For example, the antenna 158 may be disposed entirely internal of the device 101, and thus would not require fixing to the housing in this manner. Indeed, some embodiments may not even require an antenna at all. Similarly, an anchor 150 may not be required, depending on the intended application, and consequently a channel for receiving the antenna 158 need not be provided in the housing. Depending on the design of the anchor 150, the number of channels may vary, for retaining the struts of the central portion 156 of the anchor 150, or indeed for affixing other components (not shown) to the device 101.

Although the antenna is designed for use with a device to be implanted into a lumen, it may of course also be used for communication in other body parts.

With reference to the drawings in general, the function of one or more of the aspects or elements shown in the drawings may be further subdivided, and/or distributed throughout apparatus of the disclosure. In some embodiments the function of one or more elements shown in the drawings may be integrated into a single functional unit.

The above-described embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Any apparatus feature as described herein may also be provided as a method feature, and vice versa. Furthermore, equivalents and modifications not described above may also be employed without departing from the scope of the invention, which is defined in the accompanying claims.

The invention claimed is:

1. An implantable device for deployment inside a human or animal body, the device comprising:
    at least one sensing component arranged to respond to an electrical signal having a known frequency band;
    a housing arranged to house the at least one sensing component;
    at least one antenna, the at least one antenna comprising at least one antenna pole connected to the at least one sensing component, the antenna pole comprising at least one helical coil and a connecting stem;
    wherein the at least one sensing component comprises a first sensing component and a second sensing component and the at least one antenna is arranged to be in electrical communication with the first sensing component and the second sensing component; and
    the known frequency band comprises a first known frequency band and a second known frequency band different to the first known frequency band;
    wherein the first sensing component is arranged to respond to the electrical signal having the first known frequency band and the second sensing component is arranged to respond to the electrical signal having the second known frequency band; and
    wherein the helical coil and the stem are arranged so that the bandwidth of the at least one antenna encompasses the known frequency band;
    the at least one antenna being external to the housing and having a stem for securing to the housing the at least one antenna comprising an antenna insulating layer insulating it from a fluid of the body; and
    an anchor for securing the device within a vascular lumen of a human or animal body, the anchor including at least one strut for securing in a channel within the housing, the anchor comprising an anchor insulating layer insulating it from the fluid of the body;
    wherein the at least one antenna and the at least one strut of the anchor are arranged to reduce signal losses in the at least one antenna due to the at least one strut of the anchor;
    wherein the anchor is a ground structure for the at least one antenna; and
    wherein the at least one strut of the anchor is arranged to diverge or deflect at an angle of at least about 15 degrees relative to the at least one antenna.

2. The device of claim 1, wherein the at least one antenna comprises a first antenna pole and a second antenna pole;
    the first antenna pole and the second antenna pole are arranged to extend in different directions; and
    the first antenna pole and second antenna pole are arranged to be substantially coaxial.

3. The device of claim 1, wherein the at least one antenna comprises a first antenna pole and a second antenna pole;
    wherein the first antenna pole and the second antenna pole are arranged to be substantially non-coaxial;
    the second antenna pole is provided along an axis that is offset from the axis of the first antenna pole;
    the first and second antenna poles are arranged to be generally asymmetrical;
    the at least one antenna pole is completely enclosed within a sleeve;
    the sleeve is arranged to at least partially insulate the at least one antenna pole; and
    the sleeve comprises a dielectric material.

* * * * *